United States Patent
Herbert et al.

(10) Patent No.: US 8,425,492 B2
(45) Date of Patent: Apr. 23, 2013

(54) IN VIVO DEVICE, SYSTEM AND USAGE THEREOF

(75) Inventors: Michael Herbert, Wuerzburg (DE); Klaus Schilling, Wuerzburg (DE)

(73) Assignee: Julius-Maximillians-Universitaet Wuerzburg, Wuerzburg (DE)

( * ) Notice: Subject to any disclaimer, the term of this patent is extended or adjusted under 35 U.S.C. 154(b) by 405 days.

(21) Appl. No.: 12/666,095

(22) PCT Filed: Jun. 17, 2008

(86) PCT No.: PCT/EP2008/004870
§ 371 (c)(1),
(2), (4) Date: Dec. 22, 2009

(87) PCT Pub. No.: WO2009/000447
PCT Pub. Date: Dec. 31, 2008

(65) Prior Publication Data
US 2010/0189779 A1 Jul. 29, 2010

(30) Foreign Application Priority Data
Jun. 26, 2007 (EP) .................................... 07012495

(51) Int. Cl.
*A61K 9/22* (2006.01)
(52) U.S. Cl.
USPC ............... 604/890.1; 604/66; 606/27; 601/2
(58) Field of Classification Search ............. 604/65–67, 604/890.1, 891.1, 22; 600/309; 606/27; 601/2
See application file for complete search history.

(56) References Cited

U.S. PATENT DOCUMENTS

| 6,285,897 | B1 | 9/2001 | Kilcoyne |
| 6,929,636 | B1 * | 8/2005 | von Alten ............... 604/890.1 |
| 7,083,578 | B2 | 8/2006 | Lewkowicz |
| 2004/0092825 | A1 * | 5/2004 | Madar et al. ............ 600/473 |
| 2004/0193020 | A1 * | 9/2004 | Chiba et al. ............ 600/300 |

FOREIGN PATENT DOCUMENTS

| EP | 1676522 | 7/2006 |
| WO | 2006077528 | 7/2006 |

OTHER PUBLICATIONS

Sparda, et al., A novel diagnostic tool for detecting functional patency of the small bowel: the Given patency capsule Endoscopy, 37:793-800 (2005).
ISR for PCT/EP2008/004870 mailed Feb. 6, 2009.
ESR for EP7012495 mailed May 8, 2008.

* cited by examiner

*Primary Examiner* — Theodore Stigell
(74) *Attorney, Agent, or Firm* — Pabst Patent Group LLP

(57) ABSTRACT

An in vivo device (1) for an at least temporary placement in a human or animal body (17), comprising an actuator (2) adapted to be actively triggered from the exterior in order to induce a local impact on the adjacent body area for in vivo treatment of a patient in need, and/or comprising a sensor adapted to be actively triggered from the exterior for sensing a pathological condition in the body (17). An in vivo system comprises at least two and/or a plurality of the in vivo devices (1), wherein the in vivo devices (1) are adapted to communicate with each other and/or with an external controller (24). The use of the in vivo device/s (1) for treating and/or diagnosing a pathological condition in a human or animal body (17) comprises: administering the device/s (1); monitoring the movement of the device/s (1) through the body (17); triggering the device/s (1) from the outside once the device/s (1) reach/es a defined position in the body (17).

15 Claims, 7 Drawing Sheets

IN VIVO DEVICE, SYSTEM AND USAGE THEREOF

FIELD OF THE INVENTION

The invention relates to an in vivo device, an in vivo system comprising at least two or a plurality of said devices, the use of said device and of said system for in vivo treatment and diagnosis.

BACKGROUND OF THE INVENTION

Particular organs of a human or an animal body are accessible from outside via a natural body orifice for medical treatment or examination. In particular, a cavernous or tubular organ of the gastrointestinal tract like the stomach is accessible via the mouth, the oral cavity and the esophagus.

For local treatment of the stomach, the oral intake of a tablet is known. In general the tablet comprises an excipient including a pharmaceutically active agent which develops its activity in the stomach, for example to medicate gastric ulcer or intestine cancer. When a patient swallows the tablet, it passes through the oral cavity and the esophagus. The tablet needs have geometrical dimensions and an outer shape ensuring that the tablet can pass through the alimentary system without causing any harm to the patient. Further, while being transported through the oral cavity, the esophagus and the stomach, the tablet is subject to digestive secretions being chemically aggressive and tending to dissolve the tablet. Due to the acid milieu in the stomach, the passage through the stomach into the intestine is often critical so that the outer coating of the tablet must ensure that the tablet is not dissolved too early. If the tablet is dissolved in the wrong organ or cellular compartment, the pharmaceutically active ingredient is less effective or even without any desired effect.

It is also knowledge of the prior art to provide the tablet with a protective cover which encloses the excipient and the pharmaceutically active agent. The protective cover is adapted to resist digestive secretions which occur in the oral cavity, the esophagus and/or the stomach. In order to be able to release the pharmaceutically active agent in the stomach, the protective cover is additionally adapted to be dissolved by the surrounding pH conditions at the place where the pharmaceutically active substance needs to be released. However, clinical practice teaches that the composition of the gastrointestinal milieu of various patients is quite different, depending among others on further medication, nutrition and age. It remains therefore difficult to develop a protective cover which is suitable for all patients to be treated with a particular pharmaceutically active substance. Hence, it is still not possible to exactly position a tablet in an organ of a patient and trigger its decomposition at an exact time point.

To circumvent this problem, the pharmaceutically active ingredient is present in a high dosage in order to achieve the desired success of the therapy. Consequently, this may lead to undesired side effects. Further, an increase of the concentration of the pharmaceutically active agent in the tablet results in elevated costs for the tablet.

U.S. Pat. No. 7,083,578 B2 provides devices and methods for in vivo examination of a body lumen. The in vivo device comprises two operational phases, one initial phase and a second final phase. In the initial phase the device can pass freely through a normally configured body lumen, whereas is may not be able to pass freely through an abnormally configured lumen. The device may be swallowed by a person in order to reach its position inside the body.

U.S. Pat. No. 6,285,897 B1 discloses an ambulatory system for detecting, recording and analyzing gastroesophageal reflux or intraesophageal pressure. The system includes an implantable sensor and radiofrequency transmitter, an external receiver and recorder, and an analysis software package. This system provides for monitoring any of various physiological parameters, including pH, temperature, and pressure, within the esophagus or other body lumens.

EP 1 676 522 A1 discloses devices, systems and methods for locating an in vivo signal source. A system for tracking an in vivo an image sensor may include a location detecting unit to locate the in vivo image sensor over the time and a data modifying unit to modify data sampled by the location detecting unit based on information sensed by the in vivo image sensor.

Sparda et al. (2005) describe a capsule, composed of lactose which remains intact in the gastrointestinal tract for 40-100 hours post ingestion, and which disintegrates thereafter. The capsule was shown to be a safe, effective and convenient tool for assessment of functional patency of the small bowel. It could indicate functional patency even in cases where traditional radiology indicates stricture.

Thus, it is an object of the present invention to provide an in vivo device, a system and the use thereof for exactly localizing/triggering a pharmaceutically active ingredient in a patient's body for in vivo treatment and/or diagnosis.

SUMMARY OF THE INVENTION

According to the invention, this object is achieved by an in vivo device for an at least temporary placement in a human or animal body, comprising an actuator adapted to be actively triggered from the exterior in order to induce a local impact on the surrounding or adjacent body area for in vivo treatment thereof, and/or comprising a sensor adapted to be actively triggered from the exterior for sensing a pathological condition in the body.

The in vivo device is capable of being placed into the body, for example in the gastrointestinal tract. In the gastrointestinal tract the in vivo device is subject to chemically aggressive digestive secretions, which can damage or even destroy the in vivo device. Therefore, the in vivo device is provided with a protection such that the in vivo device is not destroyed or damaged by such aggressive environmental conditions.

In the gastrointestinal tract, the in vivo device is for example driven by natural movement. Therefore, when the in vivo device is administered orally and swallowed by a patient, the in vivo device passes through the gastrointestinal tract without any self propulsion. It is passively transported by the patient's gastrointestinal system. Since the in vivo device is protected against destruction mediated by the chemical surrounding, enzymes, etc., the in vivo device is transported further, until it is excreted.

When the in vivo device is located within the body, it faces an adjacent body area. However, when it is transported through the gastrointestinal tract, the in vivo device passes a predetermined body area. This area shows, for example, a pathological condition and needs to be treated and/or diagnosed. Exactly at that time point, when the in vivo device passes through/along this area or is in the vicinity thereof, the actuator of the in vivo device can to be triggered in order to induce a local impact on said area for treatment thereof.

Therefore, by triggering the actuator the impact is in a target area, and hence the impact is localized and effective. Further, other body areas which do not show this pathological condition are hardly or even not at all affected by the impact. Additionally, the extent and intensity of the impact can be specially adapted to the treatment of a particular area, which leads to a reduction of resources and saves costs.

Triggering of the impact is performed actively from the exterior. Therefore, triggering of the impact is can in a first case be performed independently of the adjacent body area the in vivo device is facing. Consequently, the timing of the external trigger of the impact cannot be affected, for example, by unpredicted local conditions. Hence, triggering the impact can be timed exactly and specifically in a target-orientated manner to the body area to be treated.

Furthermore in a second case, the sensor is adapted to be actively triggered from the exterior for sensing a pathological condition in the body. This means that triggering the sensor to sense a predetermined parameter, for example, the local temperature at a certain time at a certain location, is also exact and target-orientated. Therefore, by means of the in vivo device an exact and reliable means for sensing is provided.

Alternatively, the in vivo device can be implanted in a human or animal body. Preferred location sites are organs, like heart, kidney, stomach, gastrointestinal tract, muscles, bones etc. In this case, triggering of the impact and/or of the sensing can be performed exactly at a predetermined moment, which leads to advantages as described above.

Further, according to the invention, these objects are achieved by an in vivo system comprising at least two or a plurality of in vivo devices, wherein the in vivo devices are adapted to communicate among each other and/or with an exterior controller.

If a person administers for example at least two or the plurality of in vivo devices, each individual in vivo device is distributed over the gastrointestinal tract. Therefore as an example, at a certain moment a first in vivo device may be located in the esophagus, a second in vivo device may be located in the stomach center, a third in vivo device may be located at the pylorus and a forth in vivo device may be located in the duodenum. Since each of said in vivo devices can communicate with one or all the other in vivo devices and also with the external controller, a data processing network consisting of the at least four in vivo devices and the external controller is established. Within this network triggering of the actuators and/or the sensors can be processed. Therefore, the sensors of the second to the forth in vivo device may detect parameters, which communicate to the external controller, where triggering of the actuator of the first in vivo device is determined and communicated by means of data processing. Hence, the in vivo system advantageously establishes an elaborate triggering control for the in vivo devices.

Further, according to the invention, the above mentioned object is achieved by a method for treating and/or diagnosing a pathological condition in a human or animal body, comprising: administering the device/s; permanently monitoring the movement of the device/s through the body; and triggering the devise/s from outside once the device/s reach/es a defined position in the body. This method provides all of the above mentioned advantages.

The in vivo device, the at least two in vivo devices and/or the plurality of in vivo devices may be used as an implantable or swallowable device in a wide variety of diseases and disorders in a human or an animal. Spinal cord stimulation systems have long been accepted as a therapeutic modality for the treatment of chronic pain syndromes, and the application of tissue stimulation has begun to expand to additional applications such as angina pectoralis and incontinence. Deep brain stimulation has also been applied therapeutically for well over a decade for the treatment of refractory chronic pain syndromes, and it has also recently been applied in additional areas such as movement disorders and epilepsy. Further, in recent investigations peripheral nerve stimulation systems have demonstrated efficacy in the treatment of chronic pain syndromes and incontinence, and a number of additional applications are currently under investigation. Furthermore, functional electrical stimulation systems such as the Freehand system by NeuroControl (Cleveland, Ohio) have been applied to restore some functionality to paralyzed extremities in spinal cord injury patients. These forms of therapy may be combined with the in vivo device of the present invention.

Additionally, the in vivo device may be implanted for example into the cranium for permanent monitoring of a disease or disorder like any dysfunction of the brain, a brain tumor, intracranial pressure, head traumas (e.g., extradural hematoma, subdural hematoma, cerebral contusion, intracerebral hemorrhage, etc.), cerebrovascular accidents (e.g., intracerebral hemorrhage, cerebral infarction, cerebral apoplexy, hypoxic encephalopathy, subarachnoid hemorrhage, moyamoya disease, etc.), infections (e.g., encephalitis, AIDS encephalopathy, etc.), autoimmune diseases (e.g. systemic lupus erythematosus, etc.), and the like.

Another application of the present in vivo device is its implantation into the human or animal liver. The liver, as an important organ, performs the metabolism/detoxication of drugs and poisons by its metabolic activities. It is also important as a regulatory organ for maintaining substances necessary for maintenance of organisms, such as cholesterol, at constant concentrations in the blood. Therefore, the status of the liver may be monitored by the present in vivo device.

The in vivo device may also be used to constantly monitor a patient after medical surgery in order to ensure the patient's recovery over the time. For this the device may be administered to the patient, e.g. by injecting the device into the muscle via a needle and a syringe.

The present in vivo device may be combined with an abuse-deterrent pharmaceutical composition, which has been developed to reduce the likelihood of improper administration of drugs, especially drugs such as opioids. The drug in the in vivo device can be modified to increase its lipophilicity by forming a salt between the drug and one or more fatty acids wherein the concentration of the one or more fatty acids is one to 15 times the molar amount of the active agent, preferably two to ten times the molar amount of the active agent. The drug can be homogeneously dispersed within microparticles composed of a material that is either slowly soluble or not soluble in water. The drug may contain microparticles or drug particles which are coated with one or more coating layers, where at least one coating is water insoluble and preferably organic solvent insoluble. The abuse-deterrent composition as part of the in vivo device prevents the immediate release of a substantial portion of drug, even if the physical integrity of the formulation is compromised (for example, by chopping with a blade or crushing) and the resulting material is placed in water, snorted, or swallowed. However, when administered as directed, the drug is slowly released from the composition as part of the in vivo device as the composition is broken down or dissolved gradually within the gastrointestinal tract by a combination of enzymatic degradation, surfactant action of bile acids, and mechanical erosion.

It is preferred that the actuator is adapted to administer an active pharmaceutical ingredient, and/or to discharge a substance, and/or to emit radioactive radiation, and/or to emit sound waves, and/or to emit heat. These mechanical and/or physical actions of the actuator form the impact for treating the adjacent body area.

The active pharmaceutical ingredient may e.g. be an anti-inflammatory agent (antiphlogistic) which is administered to a patient with an inflammation, and the substance may be a contrast agent. Preferably the radioactive radiation is adapted for the treatment of a human cancer, so that cancer cells are specifically targeted. Therefore, by means of the in vivo device, a therapy can be given to a tumor.

It is preferred that the device comprises an RFID transponder which is controlled from the exterior by a controller, wherein the RFID transponder is electronically coupled to the actuator and/or the sensor for the triggering thereof. Preferably, the RFID transponder may be controlled for the outside of the body to which the in vivo device is administered.

RFID (radio frequency identification) is a non-contact transmission of data mediated by the physical basis of electromagnetic alternating field radio waves. Preferably the RFID transponder comprises a computer chip and an antenna electronically coupled thereto. The controller is adapted to transmit data to the in vivo device and/or to receive data from the in vivo device. Preferably the controller is capable of performing data processing with data received from the in vivo device and data to be transmitted to the in vivo device.

In order to transmit data from the controller to the in vivo device the controller emits radio waves received by the antenna. The radio waves carry information, for example the trigger instruction for the actuator. The radio waves are received by the antenna and induce an electric current in the antenna. The current is supplied to the computer chip which is electronically coupled to the antenna thereby providing the computer chip with power for operation and information to be processed in the computer chip. The computer chip is coupled to the actuator and/or sensor in order to transfer data thereto for triggering and/or processing. The coupling of the computer chip and the actuator and/or sensor can be realized on an electronic and/or optic basis and the like.

Advantageously RFID transponders may be manufactured and are obtainable from the manufacturing process having a particle size in a range which is convenient for oral administration.

It is preferred that the actuator and/or the sensor can be supplied with power by the RFID transponder, and/or the device comprises an internal power source, and/or an energy harvesting unit for supplying the actuator with energy.

Performing the power supply of the actuator and/or the sensor by means of the RFID transponder is advantageously, since the in vivo device does not need to contain an additional power supply unit. Receiving the energy via the antenna, the in vivo device is self-sufficiently operable and small in size.

Further, as an alternative, the provision of an internal power supply is advantageously, since the radio waves do not have to be used for power supply and consequently the energy level of the radio waves is low and therefore the level of contamination is low. As a further alternative, advantageously the in vivo device is provided with an energy harvesting unit which provides the actuator and/or the sensor with a high energy level. Nevertheless the in vivo device is small in size and the level of contamination is low. The size of the in vivo device is preferably in the range of about 2 to 5 mm. Preferred is a device with about 2 or 3 mm. If the energy harvest unit is provided, the life cycle of the in vivo device is long, since the energy supply is nearly infinite.

It is preferred that the device comprises an impermeable cover for protection. It envelopes the transponder and/or at least part of the actuator and/or the sensor.

Advantageously, the protective cover protects the in vivo device from adverse or negative environmental effects. Preferably the protective cover is realized by integrally casting the actuator and/or sensor within a protective body. If necessary, for the sake of functionality, relevant parts of the actuator and/or sensor still remain with physical contact to the outside.

It is preferred that the device comprises a capsule which encloses the actuator and which forms a first depot for storing a first substance. The in vivo device may carry the first substance. For example, the first substance can be an active pharmaceutical agent or therapeutically active drug, which is advantageously available for performing a localized treatment.

By triggering the actuator, the capsule can be made permeable such that the first substance is discharged.

Advantageously the first substance is discharged from the in vivo device by triggering the actuator. Preferably the capsule is affected from the inside, i.e. the side of the capsule which faces the actuator.

It is preferred that the first depot includes a second depot for storing a second substance, wherein the actuator is coupled to the second depot such that the second substance is releasable from the second depot into the first depot by triggering the actuator, and the capsule is adapted to be made permeable by contacting the second substance such that the first substance is released.

In a first example, the second substance can be an esterase and the capsule is made from a chemical polymer. When the actuator is triggered, it emits heat. As a consequence, the esterase is released into the first depot and is mixed with the first substance. After a certain time, the second substance reaches the capsule and contacts the inner face of the capsule. This results in the dissolution of the capsule so that the capsule becomes permeable for the first substance thereby being released.

It is preferred that the first depot includes a third depot for storing a third substance and a dividing or separation wall separating the first depot from the third depot, wherein the actuator is coupled to the dividing wall such that the dividing wall is made permeable for the first and/or second substances by triggering the actuator.

This configuration is in particular advantageous in case the first and third substances are to be stored separately for the sake of chemical stability. By making the dividing wall permeable for the first and/or third substances, in the first and third depots a mixture of the first and third substances establishes. When the dividing wall is made permeable immediately before the time the mixture comprised by the first and third substances is released into the environment of the in vivo device, the time is advantageously short during which said mixture is enclosed in the capsule.

In an alternative embodiment, the RFID device may be covered by gel-like micro- or nanospheres which are protected by an outer cover. The sizes range from about 50 nm to about 1000 nm for nanospheres and from 1 μm to 100 μm for microspheres. In the following, the term "microspheres" is used and always means "microspheres and/or nanospheres". The microspheres may carry antibodies and/or antigens on their outer surface for recognition and/or interaction with cellular counterparts, after the outer cover has been removed.

Microspheres are generally used for sustained release of drugs at constant rates. Microspheres at the outside of the RFID may be prepared with a single composition using a single mixture of a biodegradable polymer, a drug, an additive, a solvent, and the like, by a spray-drying method or other methods. From the sustained release microspheres, the release of a drug must be properly controlled at the initial phase and for a continuous period to obtain optimal pharmaceutical efficacy for a predetermined period of time. Among several biodegradable polymers used in the preparation of sustained release microspheres, the most widely used one is poly(lactide-co-glycolide) (PLGA) but polylactide (PLA), polyglycolide (PGA) or their copolymer, polyorthoesters, polyanhydrides, polyamino acids, polyhydroxybutyric acid, polycaprolactone, polyalkylcarbonate, lipids, fatty acids, waxes, and derivatives and mixtures thereof can also be used.

In another alternative, the sustained-release microspheres of the present invention may contain a short chain deoxyribonucleic acid or a short chain ribonucleic acid as the active ingredient which has been improved in the sustained-release properties and remains efficacious over a long period of time. It is intended to provide a microsphere preparation having a short chain deoxyribonucleic acid or a short chain ribonucleic acid stably encapsulated therein which can regulate the expression of a specific protein relating to a disease over a long time and can be injected or transmucosally administered.

It is preferred that the device is adapted to receive the triggering from an exterior controller and/or to perform data processing with the actuator and/or the RFID transponder.

Preferably the controller is located outside the body and is therefore accessible for operation by a person, for example a physician. By means of the controller an electromagnetic signal is sent to the RFID transponder which on its part triggers the actuator by data processing. Therefore, the actuator can be actively triggered from the exterior.

After the passage through the human or animal body, the in vivo device is excreted and forms part of the faeces. The RFIDs may be isolated by sedimentation, separation, centrifugation, filtration or the like. Alternatively, the in vivo device may be provided e.g. with a micro-magnet so that it may be easily isolated from the faeces. After isolation, the microspheres covering the RFIDs may be analyzed with respect to the data obtain from antigen antibody reactions during the passage through the human or animal body. Preferably the antigen antibody reaction may lead to a color change inside the microspheres which may be detected by standard prior art technology.

With respect to the method for treating and/or diagnosing a pathological condition in the human or animal body, it is preferred that the pathological condition is caused by a gastrointestinal disorder and it is preferred that the device/s is/are administered orally.

A further aspect of the invention is the use of an in vivo device and/or an in vivo system for treating and/or diagnosing a pathological condition in a human or an animal body. In particular, the treatment and/or the diagnosis comprise the steps of:
- administering the device/s (1) according to any of claims 1 to 11;
- monitoring the movement of the device/s (1) through the body;
- triggering the device/s from the outside once the device/s (1) reach a defined position in the body.

As mentioned above, the in vivo device and the in vivo system are advantageously used for the therapy and diagnosis of the gastrointestinal tract. For this it is convenient if the patient orally administers the in vivo device and/or the in vivo system.

BRIEF DESCRIPTION OF THE DRAWINGS

In the following the invention is explained on the basis of preferred embodiments with reference to the schematic drawings. In the drawings.

DETAILED DESCRIPTION OF PREFERRED EMBODIMENTS OF THE INVENTION

Figure 1:
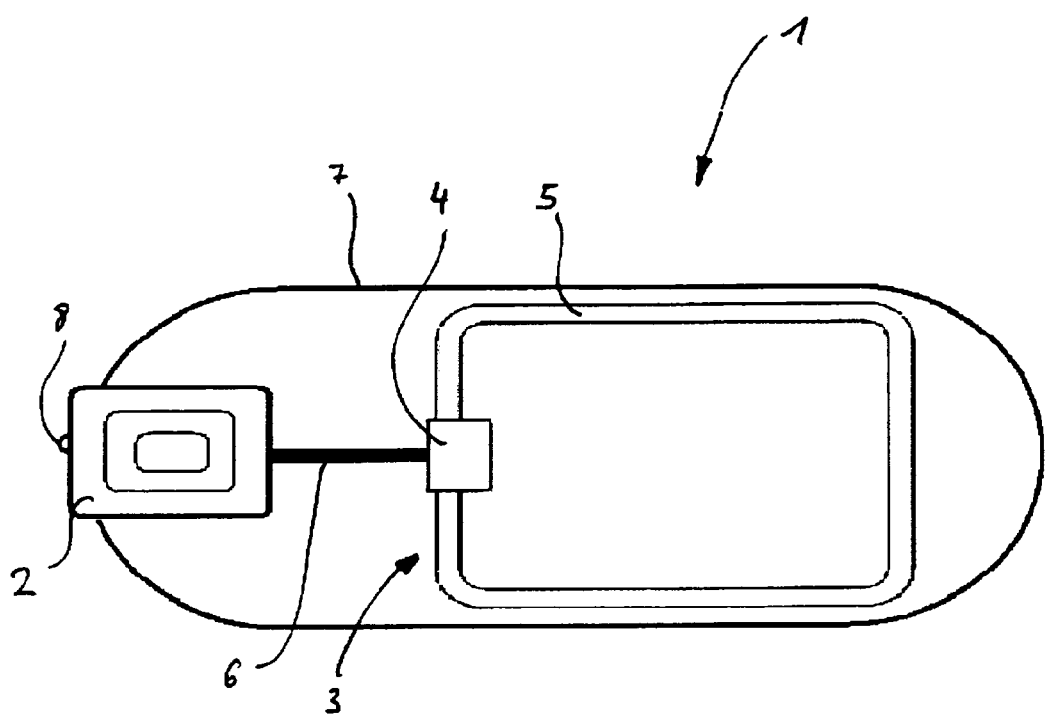
FIG. 1 is a cross-sectional view of a first embodiment of the in vivo device according to the invention.

FIG. 1 shows a first embodiment of an in vivo device 1. The in vivo device 1 comprises an actuator 2 and an RFID transponder 3. The RFID transponder 3 comprises a computer chip 4 and an antenna 5 which is connected to the computer chip 4. The antenna 5 is adapted to receive electromagnetic waves thereby supplying the computer chip 4 with energy and, if the electromagnetic wave is overlaid with an information signal, information for data processing together with the actuator 2. In order to perform the data processing between the computer chip 4 and the actuator 2, the in vivo device 1 comprises a line 6 which electronically connects the computer chip 4 and the actuator 2. The actuator 2 comprises an actuator interface 8 and is adapted to emit heat via the actuator interface 8.

Further, the in vivo device 1 comprises a protective cover 7 which envelops and covers the RFID transponder 3 and the actuator 2. However, the protective cover 7 comprises an orifice providing the actuator 2 a physical connection to the outside of the protective cover 7. The actuator 2 is arranged in the orifice such that the actuator interface 8 is facing the outside of the protective cover 7, whereas the remaining part of the actuator 2 is situated at the inside of the protective cover 7.

If the antenna 5 receives an electromagnetic wave, a current is induced in the antenna 5. The current operates the computer chip 4 processing the information signal carried by the electromagnetic wave. In case the information signal is a command for triggering heat emission of the actuator 2, the computer chip 4 is conditioned by data processing such that it controls the actuator 2 to emit heat via the actuator interface 8 towards the outside.

Figure 2:
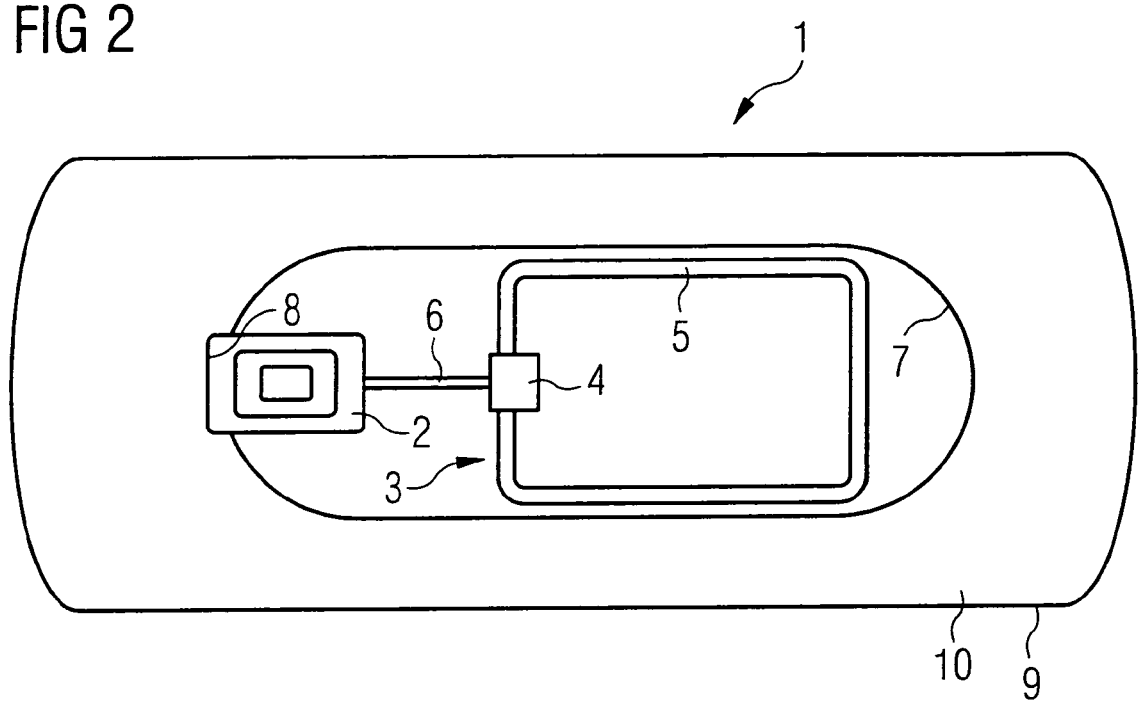
FIG. 2 is a cross-sectional view of a second embodiment of the in vivo device according to the invention.

A second embodiment of the in vivo device 1 is shown in FIG. 2. The second embodiment of the in vivo device 1 comprises the above described first embodiment. Additionally, the second embodiment of the in vivo device 1 comprises a capsule 9 which envelops and covers the protective cover 7 thereby forming a first depot 10 in a space between the capsule 9 and the protective cover 7. The first depot 10 is filled with a first substance. The first substance is contacted by the actuator interface 8.

If the antenna 5 receives an electromagnetic wave, the actuator 2 is controlled to emit heat via the actuator interface 8 to the first substance. The first substance is capable of dissolving the capsule 9 from the inside in order to break or open the capsule 9. As soon as the capsule 9 is permeable, the first substance leaves the capsule 9 to be released from the in vivo device 1.

Figure 3A:
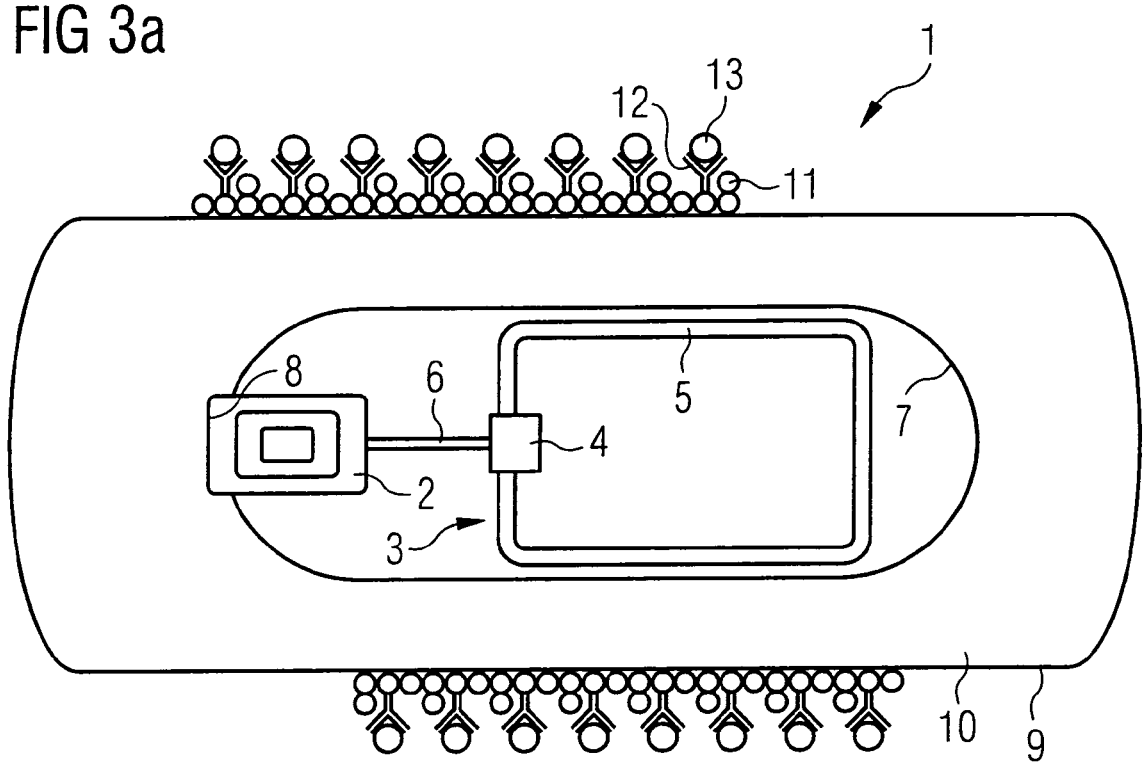
FIG. 3a is a cross-sectional view of a third embodiment of the in vivo device according to the invention.

A first alternative of a third embodiment of the in vivo device 1 is shown in FIG. 3a. This embodiment of the in vivo device 1 comprises the above described second embodiment. In this first alternative of the third embodiment, the capsule 9 of the in vivo device 1 is covered with microspheres 11. The microspheres are formed by a gel-like substance which covers the in vivo device 1. Antibodies 12 for recognition of antigens 13 are arranged on the outer surface of the microspheres 11. The antibodies 12 may have any specificity for host derived antigens, e.g. they may be specific for a certain tumor. The antibodies 12 may therefore serve for recognition of tumor markers.

Figure 3B:
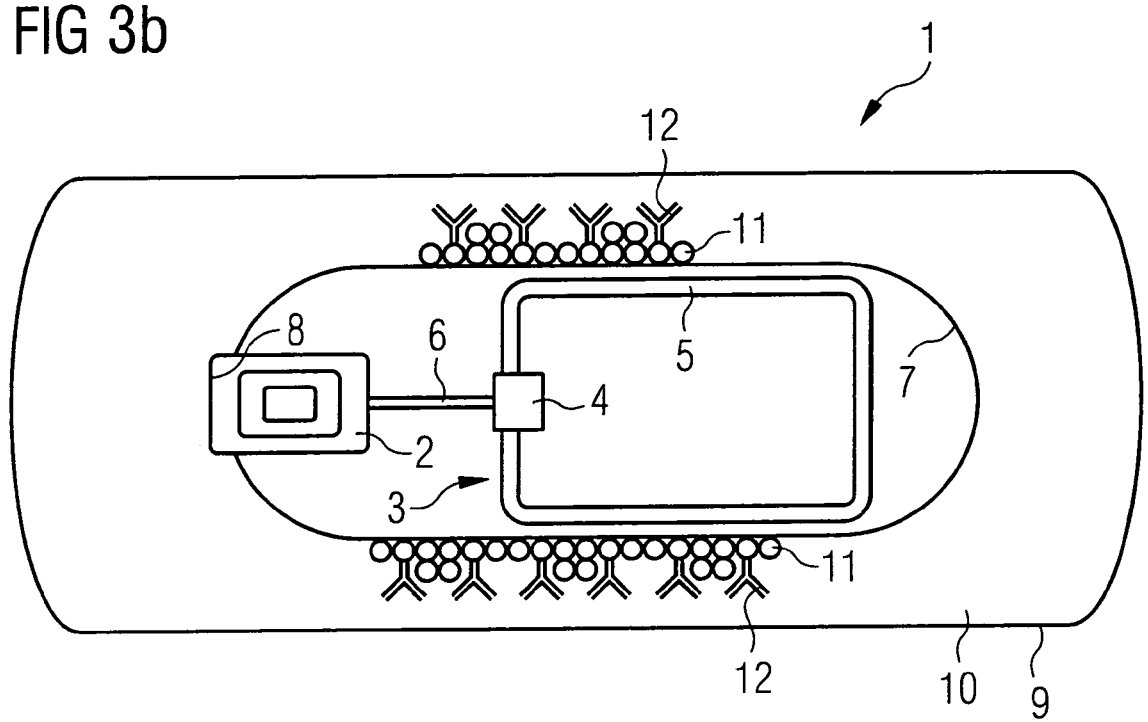
FIG. 3b is a cross-sectional view of an alternative embodiment of the third embodiment of the in vivo device according to the invention.

A second alternative of a third embodiment of the in vivo device 1 is shown in FIG. 3b. This embodiment of the in vivo device 1 also comprises the above described second embodiment. In this second alternative of the third embodiment, the microspheres 11, which carry antibodies 12, surrounds a cover 7. The antibodies 12 may either be attached directly to the cover 7 or may be attached to the microspheres 11 on the outside of the cover 7. As an outer protection layer against premature reaction of the antibodies 12 with potential targets, the capsule 9 is used.

Figure 4:
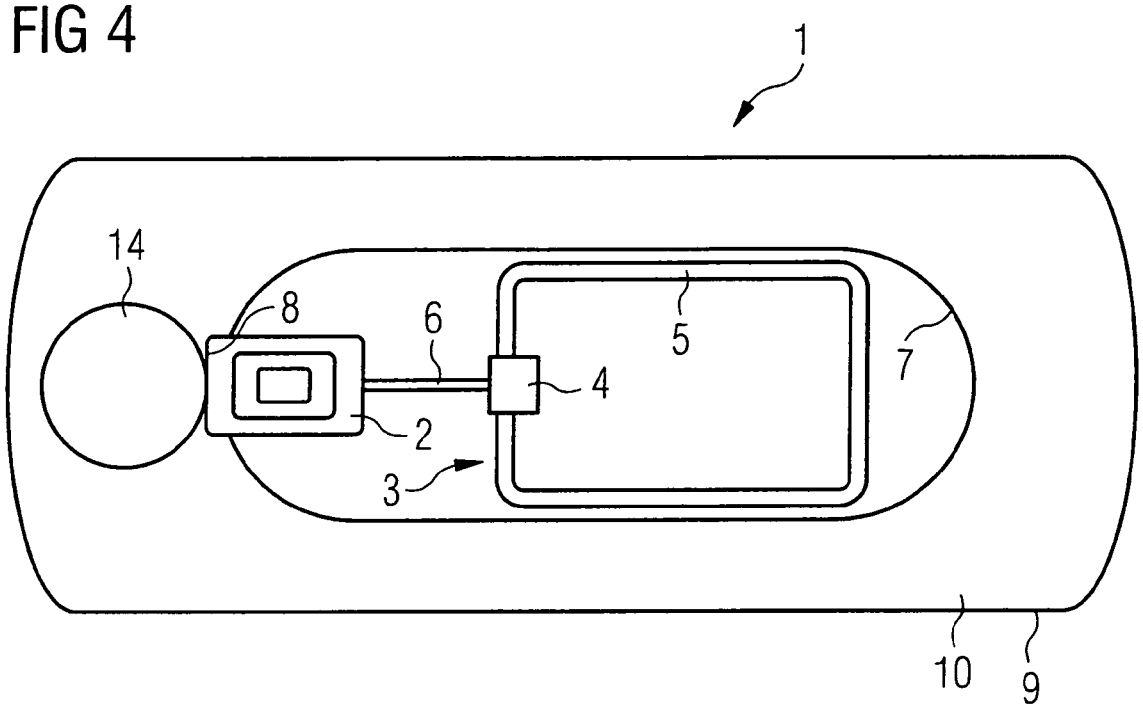
FIG. 4 is a cross-sectional view of a forth embodiment of the in vivo device according to the invention.

A forth embodiment of the in vivo device 1 is shown in FIG. 4. The forth embodiment of the in vivo device 1 comprises the above described second embodiment. Additionally, the forth embodiment of the in vivo device 1 comprises a second depot 14. The second depot 14 is designed as a cavity within the first depot 10 being arranged therein in the vicinity of the actuator interface 8 such that the actuator 2 is able to heat up the second depot 14 via the actuator interface 8 when being triggered. Within the second depot 14 a second substance is stored. The second substance is an esterase, wherein the capsule 9 is made of a polymer.

When the antenna 5 receives an electromagnetic wave, the actuator 2 is controlled to emit heat via the actuator interface 8 to the second depot. Therefore the second depot and hence the esterase is heated. As a consequence of the heat, the esterase dissolves the capsule 9, which leads to permeability and finally entire opening of the capsule 9. When the capsule 9 is opened the first substance leaves the capsule 9 and is released from the in vivo device 1.

Figure 5:
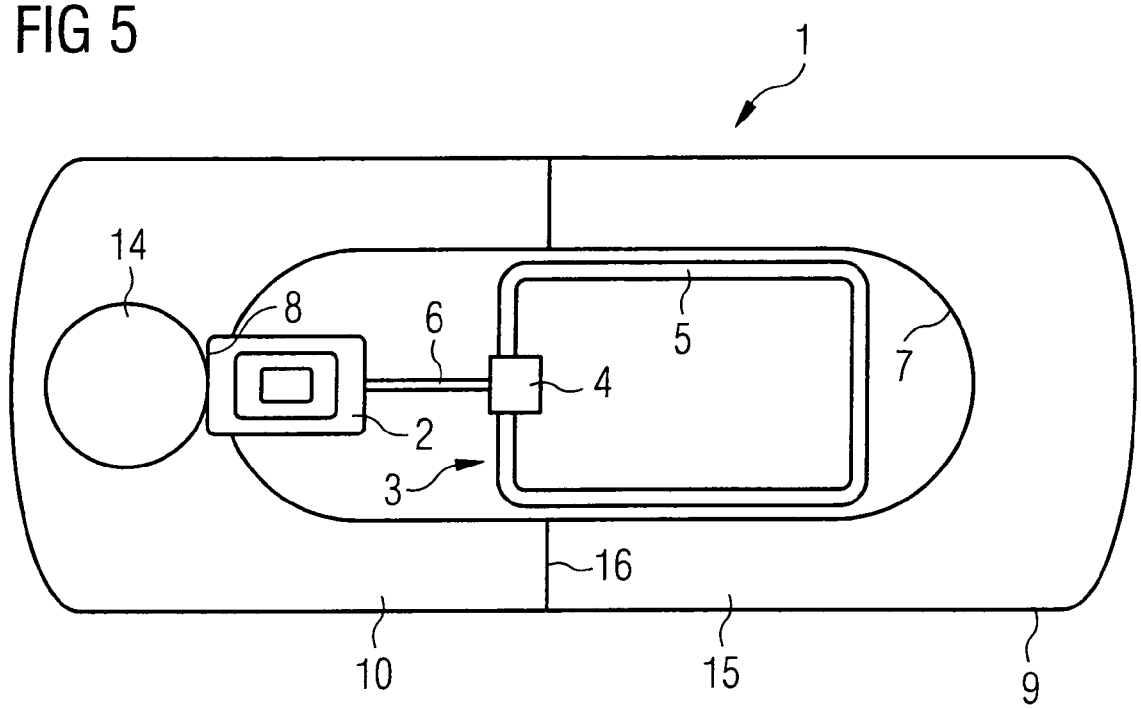
FIG. 5 is a cross-sectional view of a fifth embodiment of the in vivo device according to the invention.

A fifth embodiment of the in vivo device 1 is shown in FIG. 5. The fifth embodiment of the in vivo device 1 comprises the above described forth embodiment. Additionally, the fifth embodiment of the in vivo device 1 comprises a dividing wall 16 which separates the first depot 10 of the forth embodiment into two depots, namely the first depot 10 and the third depot 15. In the third depot 15 a third substance is stored. The dividing wall is made of a polymer. The dividing wall 16 may be permeable, semi-permeable or per se leak-proof.

Due to the dissolving activity of the esterase the dividing wall 16 is dissolved and thereby the combination and mixture of the first substance and the second substance within the capsule 9 is possible. The esterase dissolves the capsule 9 from the inside in order to open the capsule 9. Then the mixture of the first and second substance leaves the capsule 9 and is released from the in vivo device 1.

Figure 6:
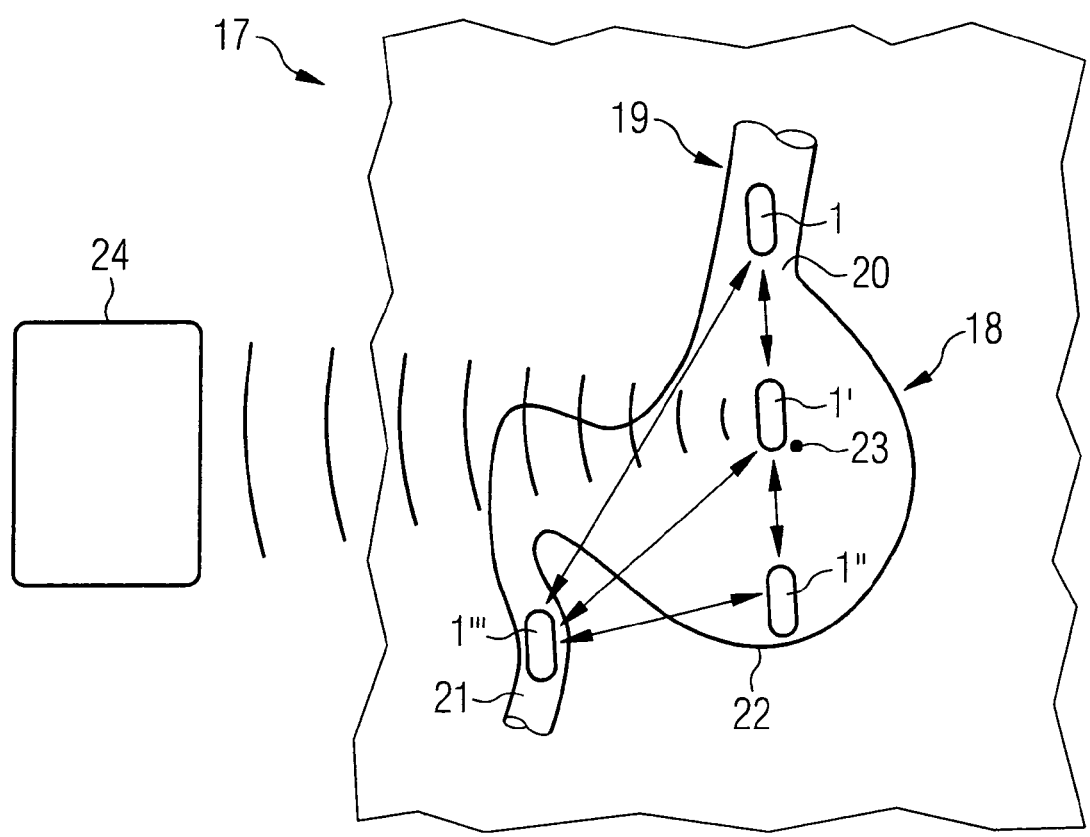
FIG. 6 is a cross-sectional view of a human body including an embodiment of the in vivo system according to the invention.

FIG. 6 shows a human body 17 with a stomach 18. The feed to the stomach 18 is formed by an esophagus 19 being located at an orifice 20 of the stomach 18. The emptying of the stomach 18 is formed into a duodenum 21. The stomach 18 comprises a stomach centre 23 and a bottom formed by a stomach fundus 22.

Within the human body 17 four in vivo devices 1, 1', 1", 1''' forming a network, are arranged in the following way: The first in vivo device 1 is arranged in the esophagus 19 at the orifice 20 of the stomach 18. The second in vivo device 1' is arranged in the stomach centre 23. The third in vivo device 1" is arranged at the stomach fundus 22. The forth in vivo device 1''' is arranges in the duodendum 21.

A controller 24 is located outside the human body 17. The controller 24 is adapted such that the electromagnetic wave (indicated in FIG. 6 with circle lines) can be emitted manually or automatically. The antenna 5 and the controller 24 are designed such that the electromagnetic wave generated by the controller can penetrate the human body 17 which is then received by the antenna 5.

As shown in FIG. 6, the electromagnetic wave is sent to the second in vivo device 1'. The antenna 5 of the second in vivo device 1' receives the electromagnetic wave and triggers the actuator 5 of the second in vivo device 1'. For example, the second in vivo device 1' may be according to the third embodiment. Then, when the actuator 5 of the second in vivo device 1' is triggered, the first substance of the second in vivo device 1' is released to the stomach centre 23.

The in vivo devices 1, 1', 1", 1''' are adapted to perform communication among themselves, which is shown in FIG. 6 by arrows. The communication is based on data transfer among at least two of the in vivo devices 1, 1', 1", 1'''. The data transfer is accomplished by the use of electromagnetic waves.

Therefore, triggering the actuator 5 of one of the in vivo devices 1, 1', 1", 1''' can be influenced by the controller 24 and/or the other in vivo devices 1, 1', 1", 1'''.

For example, the second in vivo device 1' comprises a sensor which may be triggered like its actuator 2. The sensor is adapted to detect the pH-value of the medium surrounding the second in vivo device 1'. Since the second in vivo device 1' is located in the stomach centre 23, the sensor of the second in vivo device 1' detects the pH-value in the stomach centre 23.

For example, the detection of the pH-value by the sensor can be triggered by the electromagnetic wave. Hence, by operating the controller 24 accordingly, the electromagnetic wave is sent to the second in vivo device 1' thereby triggering the sensor. Consequently, at that time the sensor determines the pH-value in the stomach centre 23. The second in vivo device 1' is adapted such that the sensor transmits the determined pH-value to the computer chip 4 which processes the data based on the determined pH-value. The computer chip 4 of the second in vivo device 1' is configured such that, in case the determined pH-value exceeds a predetermined pH-value, the actuator 2 of the second in vivo device 1' sends a trigger signal to the other in vivo devices 1, 1", 1''' in order to trigger their actuators 2. The triggering of these actuators 2 leads to a release of the first substance by the first in vivo device 1 in the esophagus 19 at the orifice 20 of the stomach 18, by the third in vivo device 1" at the stomach fundus 22, and by the forth in vivo device 1''' in the duodendum 21.

The above described configuration is exemplary. All conceivable configurations shall be included in the disclosure.

REFERENCE CHARACTER LIST 1, 1', 1", 1''' in vivo device
2 actuator
3 RFID transponder
4 computer chip
5 antenna
6 line
7 protective cover
8 actuator interface
9 capsule
10 first depot
11 microsphere/nanosphere
12 antibody
13 antigen
14 second depot
15 third depot
16 dividing wall
17 human body 18 stomach
19 esophagus
20 orifice of stomach
21 duodenum
22 stomach fundus
23 stomach centre
24 controller

REFERENCE LIST

Patent Literature

U.S. Pat. No. 7,083,578 B1 to Lewkowski
U.S. Pat. No. 6,285,897 B1 to Kilcoyne et al.
EP 1 676 522 A1 to Horn Non-Patent Literature Sparda C. et al., Endoscopy 2005; 37: 797-800

The invention claimed is:

1. An in vivo device (1) for an at least temporary placement in a human or animal body (17), comprising an actuator (2) and an RFID transponder (3), which is controlled from the exterior of the body, wherein the RFID transponder (3) is electronically coupled to the actuator (2), such that the actuator is actively triggered from the exterior in order to induce a local impact on the adjacent body area for in vivo treatment thereof, and an impermeable protective cover (7), which covers the RFID transponder (3) and/or at least part of the actuator (2), and a capsule (9), which encloses the actuator (2) and which envelops the protective cover (7) and which forms a first depot (10) for storage of a first substance, wherein the capsule (9) is adapted to be made permeable by triggering the actuator (2) such that the first substance is released.

2. The device (1) according to claim 1, wherein the actuator (2) is adapted to discharge a substance, and/or to emit radioactive radiation, and/or to emit sound waves, and/or to emit heat.

3. The device (1) according to claim 1, further comprising a sensor, wherein the RFID transponder (3) is electronically coupled to the sensor, such that the sensor is actively triggered from the exterior for sensing a pathological condition in the body (17).

4. The device (1) according to claim 3, wherein the protective cover (7) covers at least part of the sensor.

5. The device (1) according to claim 1, wherein the actuator (2) and/or the sensor is/are supplied with power by the RFID transponder (3), and/or the device (1) comprises an internal power source, and/or an energy harvesting unit for supplying the actuator (2) with energy.

6. The device (1) according to claim 1, wherein the first depot (10) includes a second depot (14) for storage of a second substance, wherein the actuator (2) is coupled to the second depot (14) such that the second substance is releasable from the second depot (14) into the first depot (10) by triggering the actuator (2), and the capsule (9) is adapted to be made permeable by contacting the second substance such that the first substance is released.

7. The device (1) according to claim 6, wherein the first depot (10) includes a third depot (15) for storing a third substance and a dividing wall (16), which separates the first depot (10) from the third depot (15), wherein the actuator (2) is coupled to the dividing wall (16) such that the dividing wall (16) is made permeable for the first and/or second substances by triggering the actuator (2).

8. The device (1) according to claim 7, wherein the first substance, the third substance and/or a mixture thereof is an active pharmaceutical agent or a therapeutically active drug.

9. The device (1) according to claim 7, wherein the first substance is an active pharmaceutical agent or a therapeutically active drug and the third substance is an active pharmaceutical agent.

10. The device (1) according to claim 6, wherein the second substance is an esterase and the capsule (9) is made from a chemical polymer, such that the esterase degrades the chemical polymer.

11. The device (1) according to claim 10, wherein the actuator (2) when triggered emits heat via an actuator interface (8) to the second depot (14) thereby heating the esterase and as a consequence, the esterase dissolves the capsule (9).

12. The device (1) according to claim 1, wherein microspheres (11) cover the capsule (9) and antibodies (12) and/or antigens (13) are located on the micro spheres (11).

13. The device (1) according to claim 1, wherein microspheres (11) with antibodies (12) are located on a cover (7) and are protected by the capsule (9).

14. The device (1) according to claim 1, wherein the device (1) is adapted to receive a trigger from an exterior controller (24) or to perform data processing with the actuator (2) or the RFID transponder.

15. An in vivo system comprising at least two of in vivo devices (1) according to claim 1, wherein the in vivo devices (1) are adapted to communicate with each other and/or with an exterior controller (24).

* * * * *

UNITED STATES PATENT AND TRADEMARK OFFICE
CERTIFICATE OF CORRECTION

PATENT NO. : 8,425,492 B2  Page 1 of 1
APPLICATION NO. : 12/666095
DATED : April 23, 2013
INVENTOR(S) : Herbert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 403 days.

Signed and Sealed this
Eighth Day of September, 2015

Michelle K. Lee
*Director of the United States Patent and Trademark Office*